United States Patent [19]
Cannizzo et al.

[11] Patent Number: 5,723,604
[45] Date of Patent: Mar. 3, 1998

[54] SYNTHESIS OF 2,4,6,8,10,12-HEXABENZYL-2, 4,6,8,10,12-HEXAAZATETRACYCLO [5.5.0.0$^{5,9}$.0$^{3,11}$]DODECANE

[75] Inventors: Louis F. Cannizzo, Ogden; William W. Edwards, Tremonton; Robert B. Wardle, Logan; Thomas K. Highsmith, North Ogden, all of Utah

[73] Assignee: Thiokol Corporation, Ogden, Utah

[21] Appl. No.: 493,627

[22] Filed: Jun. 22, 1995

[51] Int. Cl.$^6$ .................................................. C07D 487/22
[52] U.S. Cl. .................................................. 540/556
[58] Field of Search .................................................. 540/556

[56] References Cited

U.S. PATENT DOCUMENTS

| | | | |
|---|---|---|---|
| 2,582,128 | 2/1952 | Hurwitz | 260/566 |
| 2,987,522 | 6/1961 | Shen | 260/309.6 |
| 3,024,236 | 3/1962 | Hughes | 260/256.4 |
| 3,959,277 | 5/1976 | Donald | 260/250 |

OTHER PUBLICATIONS

Nielsen et al., *Polyazapolycyclics by Condesation of Aldehydes with Amines. 2. Formation of 2,4,6,8,10,12–Hexabenzyl–2,4,6,8,10,12–hexaazatetracyclo[5.5.0.0$^{5,9}$.0$^{3,11}$] dodecanes from Glyoxal and Benzylamines*[1,2], Journal of Organic Chemistry, pp. 1459–1466, vol. 55, No. 5 (1990).

Crampton, M.R. et al. *J. Chem. Soc. Perkin Trans. II*, pp. 923–929 (1993).

Brown, T.L. et al *Chemistry. The Central Science* (Prentice-Hall, N.J.), pp. 450, 451, 456–458, 463 and 464 (1981).

*Primary Examiner*—Mukund J. Shah
*Assistant Examiner*—King Lit Wong
*Attorney, Agent, or Firm*—Cushman Darby & Cushman Ip Group of Pillsbury; Madison & Sutro, LLP; Ronald L. Lyons, Esq.

[57] ABSTRACT

A process of synthesizing HBIW using a mineral acid, such as perchloric acid, as the acid catalyst is disclosed. According to the process, glyoxal, adjusted to a pH from 4 to 7, and benzylamine are reacted in the presence of the mineral acid for sufficient time to form HBIW. The resulting HBIW is then isolated according to conventional separation techniques.

35 Claims, No Drawings

SYNTHESIS OF 2,4,6,8,10,12-HEXABENZYL-2, 4,6,8,10,12-HEXAAZATETRACYCLO [5.5.0.05, 9.03,11]DODECANE

GOVERNMENT RIGHTS

The U.S. Government has a certain rights in this invention as provided for by the terms of contract No. N00014-91-C-0254 awarded by the Office of Naval Research.

FIELD OF THE INVENTION

The present invention relates to an improved synthesis of 2,4,6,8,10,12-hexabenzyl-2,4,6,8,10,12-hexaazatetracyclo [5.5.0.0$^{5,9}$.0$^{3,11}$]dodecane, sometimes referred to as "hexabenzyl-hexaazaisowurtzitane" and hereinafter referred to as "HBIW."

BACKGROUND OF INVENTION

An important step in the synthesis of 2,4,6,8,10,12-hexanitro-2,4,6,8,10,12-hexaazatetracyclo[5.5.0.0$^{5,9}$0$^{3,11}$]-dodecane, sometimes referred to as "HNIW" or "CL-20," is the synthesis of the chemical intermediate, HBIW. An improvement to the synthesis of HBIW would represent an improvement in the overall synthesis of CL-20. CL-20 is a new polycyclic caged nitramine oxidizer. For most existing weapons systems, the most critical ingredient in both propellant and explosive applications is the oxidizer. CL-20, with its substantial increase in performance output, represents a major break-through in energy capabilities for future propellant and explosive systems. It may be possible to replace existing weapons system energetic fills with CL-20 to increase shaped charge anti-armor penetration, increase missile payload velocity and standoff, increase underwater torpedo effectiveness and lethality, and improve gun propellant impetus.

The currently known technique of synthesizing HBIW is reported by Nielsen et al., "Polyazapolycyclics by Condensation of Aldehydes with Amines. 2. Formation of 2,4,6,8, 10,12-hexabenzyl-2,4,6,8,10,12-hexaazatetracyclo[5.5.0 .0$^{5,9}$.0$^{3,11}$]dodecanes from Glyoxal and Benzylamines," *Journal of Organic Chemistry*, vol. 55, pp. 1459–1466, 1990, which is incorporated herein by reference. According to Nielsen et al., HBIW is synthesized by reaction of benzyl amine and glyoxal using formic acid as a catalyst. This reaction is shown below:

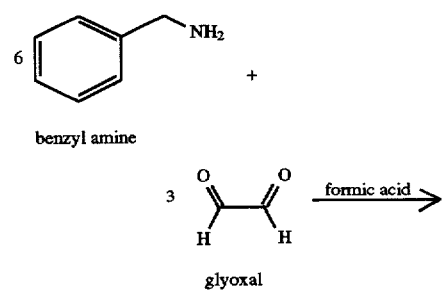

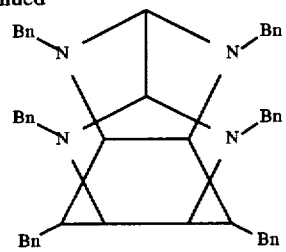

HBIW

In the Nielsen et al. process, HBIW is prepared by condensation of a slight stoichiometric excess of benzylamine with 40% aqueous glyoxal in aqueous acetonitrile solvent (15% total water) at 25° C. An acid catalyst (formic acid, 10 molar % of the amine) is required. The reaction is reported to be rapid and nearly complete within a few hours. The crystalline product is recovered by filtration.

In pilot plant-scale runs of this process performed by Thiokol Corporation, Aerojet, and NAWC, the isolated yield of HBIW was in the range of 55% to 65%. Such yields may be acceptable for small scale production of CL-20, but if substantial quantities (i.e., in excess of 1000 pounds per year) are desired, then significant improvements to the process are required. Thus, it would be an important advancement in the art to provide a process for synthesizing HBIW which greatly improves the yield of HBIW.

Such process for synthesizing HBIW is disclosed and claimed herein.

SUMMARY OF THE INVENTION

The present invention is directed to a process of synthesizing HBIW using a mineral acid as the acid catalyst. According to the present invention, glyoxal and benzylamine are reacted in the presence of the mineral acid for sufficient time to form HBIW. The resulting HBIW is then isolated according to conventional separation techniques. When compared to a baseline process using formic acid, the process of synthesizing HBIW using perchloric acid as the acid catalyst produced up to a 31% increase in the yield of HBIW, with typical yield increases of 10–15%. This represents a substantial improvement over the current process.

The glyoxal is preferably slowly added to a reaction solution containing the benzylamine and the mineral acid. For reproducible yields, the pH of the glyoxal is adjusted (with addition of a small quantity of aqueous sodium bicarbonate or another suitable aqueous base such as $Na_2CO_3$, $K_2CO_3$, $KHCO_3$, NaOH, KOH, etc.) in the range from about 4 to 7, and most preferably in the range from about 5 to 6. This adjustment is performed before adding the glyoxal to the mixture. The reaction solution includes a polar organic solvent which is substantially nonreactive with the glyoxal and benzylamine. For best yields of HBIW, the temperature of the reaction solution is preferably less than 20° C., and more preferably less than 10° C. It is currently preferred to use a slight stoichiometric excess of benzylamine in the process.

Although only a small amount of mineral acid is needed to catalyze the reaction, good yields are obtained when the molar ratio of mineral acid to benzylamine is in the range from about 0.01 to about 0.2.

DETAILED DESCRIPTION OF THE INVENTION

The present invention is directed to a process of synthesizing HBIW. In the process, formic acid is replaced by a mineral acid as the acid catalyst. According to the present invention, glyoxal and benzylamine are reacted in the presence of a mineral acid for sufficient time to form HBIW. Perchloric acid is the currently preferred mineral acid, although other common mineral acids such as sulfuric acid, hydrochloric acid, and nitric acid may also be used. The resulting HBIW is then isolated according to conventional separation techniques.

In the currently preferred process, the glyoxal is added to a reaction solution containing the benzylamine and the perchloric acid. The reaction solution must contain a polar organic solvent which is substantially nonreactive with glyoxal and benzylamine. Several polar organic solvents may be used in the present invention such as acetonitrile, nitromethane, methanol, ethanol, and tetrahydrofuran. Wet acetonitrile is the presently preferred polar organic solvent.

The temperature of the reaction solution during glyoxal addition affects the yield of HBIW. Higher yields are obtained at lower temperatures. The reaction solution during glyoxal addition is preferably chilled at a temperature less than about 20° C., and more preferably at a temperature less than about 10° C., and most preferably at a temperature in the range from about 5° C. to 10° C.

It has also been observed that higher yields of HBIW are obtained when glyoxal is added slowly to the reaction solution. The glyoxal is preferably added to the reaction solution over a time period from about 10 minutes to about 4 hours and more preferably over a time period greater than 2 hours. If the glyoxal is added too quickly, then unwanted polymerization products are obtained. Moreover, when large scale batches of HBIW are prepared, slower addition of glyoxal helps achieve more uniform mixing.

The quantity of glyoxal and benzylamine used in the reaction may range from approximately stoichiometric quantities to a moderate stoichiometric excess of benzylamine. Excess glyoxal should be avoided, otherwise large amounts of unwanted polymerization products will likely be formed.

Only a small amount of mineral acid is needed to catalyze the reaction. In fact, HBIW may be obtained at low yields without any acid to catalyze the benzyl amine protonation. However, highest yields are obtained when the mineral acid is perchloric acid and the molar ratio of perchloric acid to benzylamine is in the range from about 0.01 to about 0.2. Defined in other terms, the weight ratio of benzylamine to perchloric acid is preferably in the range from about 5:1 to about 100:1.

The pH of the glyoxal mixture before addition to the reaction solution also affects yield. The glyoxal mixture pH is preferably in the range from about 4 to 7, and most preferably in the range from about 5 to 6. Not wishing to be bound by theory, it is presently believed that the 40% aqueous glyoxal normally contains small quantities of acid (probably glyoxalic acid) which lead to variable yields. Addition of aqueous sodium bicarbonate neutralizes the acids and leads to reproducible yields.

Although the HBIW is preferably isolated by filtration, those skilled in the art will appreciate that other isolation techniques commonly used in chemical synthesis, such as centrifugation and decanting may be used instead of filtration.

The present invention is further described in the following nonlimiting examples.

EXAMPLE 1

To establish a baseline yield for formic acid-catalyzed HBIW manufacture, the following procedure was employed.

In a 200 mL jacketed flask equipped with a magnetic stir bar, was added 10 mL of water, 110 mL of acetonitrile, 0.49 mL of formic acid, and 11.8 grams of benzyl amine. The resulting mixture was stirred and cooled to 15° C. To this stirred mixture was added a 7.25 grams of 40% by weight glyoxal (in water) dropwise over a 10 to 30 minute period. Stirring was continued at 15° C. for an additional 18 hours. The mixture was then filtered, and the solids obtained washed with 50 mL of cold acetonitrile, and allowed to dry under an air flow for several hours. The purity of the white powdery solid obtained was checked by proton NMR analysis. In three identical experiments, the yields of solid obtained were 6.90 grams, 6.81 grams, and 6.80 grams. This gives an average yield of 6.84 grams of HBIW. A quantitative yield of HBIW, based on the limiting reagent glyoxal, would be 11.80 grams. Therefore, the isolated yield was 58% of theoretical. This value is within the yield range reported for the pilot plant-scale process. Using the same procedure, different lots of glyoxal gave variable yields up to a maximum of 63%.

EXAMPLE 2

To determine the yield of perchloric acid-catalyzed HBIW manufacture, the procedure of Example 1 was repeated two times, replacing the formic acid with 0.96 mL of 70% by weight perchloric acid (in water). The same lots of the other reagents were employed in the same reaction apparatus. The weights of HBIW obtained were 9.00 grams and 8.98 grams, which gives an average yield of 8.99 grams of HBIW. This corresponds to an isolated yield of 76% of theoretical. Compared to the baseline yield of Example 1, this represents a 31% increase in the quantity of HBIW isolated from the procedure.

Using the same procedure, different lots of glyoxal gave variable yields of HBIW to as low as 65%. However, it was found that reproducible yields of HBIW (68% to 71%) could be obtained when the pH of the glyoxal solution was adjusted to a pH of 4 to 7 (preferably 5 to 6), employing aqueous sodium bicarbonate, before the glyoxal was added to the mixture. By comparison, under these same conditions, formic acid catalyst afforded a 62% yield.

Other mineral acid catalysts including nitric acid, sulfuric acid, and hydrochloric acid were also found to be effective acid catalysts to form HBIW by the methods listed herein, although perchloric acid gave the highest yields of HBIW.

These additional experiments are summarized in Table 1 below. In all cases, 50 mmol glyoxal in 10 mL water were reacted with 110 mmol benzylamine and 11 mmol of an acid catalyst in 110 mL of $CH_3CN$ solvent.

TABLE 1

| Example | pH glyoxal | acid catalyst | % yield |
| --- | --- | --- | --- |
| 3 | ? | $HClO_4$ | 65 |
| 4 | ? | $H_2SO_4$ | 50 |
| 5 | ? | HCl | 66 |
| 6 | ? | $HNO_3$ | 65 |
| 7 | ? | HCl | 64 |
| 8 | ? | HCOOH | 63 |
| 9 | ? | HCOOH | 63 |
| 10 | ? | $HClO_4$ | 68 |
| 11* | ? | $HClO_4$ | 66 |
| 12 | ? | $HClO_4$ | 65 |
| 13 | 7** | $HClO_4$ | 66 |
| 14 | 4.6 | $HClO_4$ | 70 |
| 15 | 3 | $HClO_4$ | 61 |

TABLE 1-continued

| Example | pH glyoxal | acid catalyst | % yield |
|---------|------------|---------------|---------|
| 16 | 4 | HClO$_4$ | 68 |
| 17 | 6 | HClO$_4$ | 70 |
| 18 | 5 | HClO$_4$ | 71 |
| 19 | 7 | HClO$_4$ | 69 |
| 20 | 5 | HCOOH | 61 |
| 21 | 5 | HCOOH | 62 |
| 22 | 5 | HClO$_4$ | 69 |
| 23 | 5 | HCl | 60 |
| 24 | 5 | HNO$_3$ | 67 |

*Reaction temperature of 10° C.
**Used 1:1 mixture of glyoxal solution and bicarbonate solution.

From the foregoing, it will be appreciated that the present invention provides a process for synthesizing HBIW which improves the yield of HBIW.

The present invention may be embodied in other specific forms without departing from its essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The claimed invention is:

1. A process of synthesizing 2,4,6,8,10,12-hexabenzyl-2,4,6,8,10,12-hexaazatetracyclo[5.5.0.0$^{5,9}$.0$^{3,11}$] dodecane ("HBIW") comprising the steps of:

(a) adjusting the pH of a glyoxal solution containing glyoxal to a pH of from 5 to 6;

(b) reacting said aqueous glyoxal solution and benzylamine in the presence of a mineral acid for sufficient time to form HBIW, wherein the glyoxal solution and benzylamine are in a polar organic solvent which is substantially nonreactive with glyoxal and benzylamine; and (c) isolating the HBIW.

2. A process of synthesizing HBIW as defined in claim 1, wherein the mineral acid is selected from perchloric acid, sulfuric acid, hydrochloric acid, and nitric acid.

3. A process of synthesizing HBIW as defined in claim 1, wherein the polar organic solvent contains acetonitrile.

4. A process of synthesizing HBIW as defined in claim 1, wherein the quantity of glyoxal and benzylamine are approximately stoichiometric.

5. A process of synthesizing HBIW as defined in claim 1, wherein a stoichiometric excess of benzylamine is used in the process.

6. A process of synthesizing HBIW as defined in claim 1, wherein the mineral acid is perchloric acid and the molar ratio of perchloric acid to benzylamine is in the range from about 0.01 to about 0.2.

7. A process of synthesizing HBIW as defined in claim 1, wherein the mineral acid is percloric acid and the weight ratio of benzylamine to perchloric acid is in the range from about 5:1 to about 100:1.

8. A process of synthesizing HBIW as defined in claim 1, wherein the reacting step occurs at a temperature less than about 20° C.

9. A process of synthesizing HBIW as defined in claim 1, wherein the reacting step occurs at a temperature less than about 10° C.

10. A process of synthesizing HBIW as defined in claim 1, wherein the HBIW is isolated by filtration.

11. A process of synthesizing HBIW as defined in claim 1, wherein the pH of the glyoxal solution is adjusted using an aqueous solution of sodium bicarbonate prior to reacting with the benzylamine.

12. A process of synthesizing HBIW as defined in claim 1, wherein the pH of the glyoxal solution is adjusted using at least one aqueous base selected from the group consisting of Na$_2$CO$_3$, KHCO$_3$, NaOH and KOH.

13. A process of synthesizing HBIW as defined in claim 1, wherein the mineral acid is selected from the group consisting of perchloric acid, sulfuric acid, hydrochloric acid, and nitric acid;

said polar organic solvent contains acetonitrile;

the molar ratio of said mineral acid to benzylamine is in the range of about 0.01 to about 0.20; and the temperature during said glyoxal addition step is less than about 10° C.

14. A process of synthesizing 2,4,6,8,10,12-hexabenzyl-2,4,6,8,10,12-hexaazatetracyclo[5.5.0.0$^{5,9}$.0$^{3,11}$]dodecane ("HBIW") comprising the steps of:

(a) providing an aqueous glyoxal solution containing glyoxal, said solution having a pH of from 4 to 7;

(b) adding said aqueous glyoxal to a reaction solution containing benzylamine, perchloric acid, and a polar organic solvent which is substantially nonreactive with the glyoxal and the benzyl amine;

(c) allowing the glyoxal and the benzylamine to react and form HBIW; and (d) isolating the HBIW.

15. A process of synthesizing HBIW as defined in claim 14, wherein the polar organic solvent contains acetonitrile.

16. A process of synthesizing HBIW as defined in claim 14, wherein the glyoxal is added to the reaction solution over a time period from about 10 minutes to about 4 hours.

17. A process of synthesizing HBIW as defined in claim 14, wherein the glyoxal is added to the reaction solution over a time period greater than about 2 hours.

18. A process of synthesizing HBIW as defined in claim 14, wherein the reaction solution is chilled during glyoxal addition.

19. A process of synthesizing HBIW as defined in claim 14, wherein the reaction solution has a temperature less than about 10° C. during glyoxal addition.

20. A process of synthesizing HBIW as defined in claim 14, wherein the quantity of glyoxal and benzylamine are approximately stoichiometric.

21. A process of synthesizing HBIW as defined in claim 14, wherein a stoichiometric excess of benzylamine is used in the process.

22. A process of synthesizing HBIW as defined in claim 14, wherein the molar ratio of perchloric acid to benzylamine is in the range from about 0.01 to about 0.2.

23. A process of synthesizing HBIW as defined in claim 14, wherein the weight ratio of benzylamine to perchloric acid is in the range from about 5:1 to about 100:1.

24. A process of synthesizing HBIW as defined in claim 14, wherein the HBIW is isolated by filtration.

25. A process of synthesizing HBIW as defined in claim 14, wherein the pH of the aqueous glyoxal is adjusted using an aqueous solution of sodium bicarbonate prior to addition into the reaction solution.

26. A process of synthesizing HBIW as defined in claim 14, wherein the pH of the aqueous glyoxal is adjusted to a pH from 5 to 6.

27. A process of synthesizing HBIW as defined in claim 14, wherein the pH the glyoxal solution having a pH of 4 to 7 is obtained by treating a glyoxal solution with at least one aqueous base selected from the group consisting of $Na_2CO_3$, $KHCO_3$, NaOH and KOH.

28. A process for neutralizing HBIW as defined in claim 16, wherein the reaction solution is chilled during glyoxal addition; the molar ratio of perchloric acid to benzylamine is in the range from about 0.01 to about 0.2; and the aqueous glyoxal solution having a pH of 4 to 7 in (a) is obtained by treating a glyoxal solution with at least one aqueous base selected from the group consisting of $Na_2CO_3$, $KHCO_3$, NaOH and KOH.

29. A process of synthesizing 2,4,6,8,10,12-hexabenzyl-2,4,6,8,10,12-hexaazatetracyclo[$5.5.0.0^{5,9}.0^{3,11}$]dodecane ("HBIW") comprising the steps of:

(a) adjusting the pH of a glyoxal solution containing glyoxal to a pH from 4 to 7 with aqueous sodium bicarbonate;

(b) adding the glyoxal solution into a chilled reaction solution containing benzylamine, perchloric acid, and a polar organic solvent which is substantially nonreactive with the glyoxal and the benzylamine, wherein the polar organic solvent contains acetonitrile and water, wherein the glyoxal solution is added to the reaction solution over a time period from about 10 minutes to about 4 hours;

(c) allowing the glyoxal and the benzylamine to react and form HBIW; and (d) isolating the HBIW by filtration.

30. A process of synthesizing HBIW as defined in claim 29, wherein the reaction solution has a temperature less than about 10° C. during glyoxal solution addition.

31. A process of synthesizing HBIW as defined in claim 29, wherein a stoichiometric excess of benzylamine is used in the process.

32. A process of synthesizing HBIW as defined in claim 29, wherein the molar ratio of perchloric acid to benzylamine is in the range from about 0.01 to about 0.2.

33. A process of synthesizing HBIW as defined in claim 29, wherein the weight ratio of benzylamine to perchloric acid is in the range from about 5:1 to about 100:1.

34. A process of synthesizing HBIW as defined in claim 29, wherein the pH of the glyoxal solution is adjusted to a pH from 5 to 6.

35. A process of synthesizing 2,4,6,8,10,12-hexabenzyl-2,4,6,8,10,12-hexaazatetracyclo[$5.5.0.0^{5,9}.0^{3,11}$]dodecane ("HBIW") comprising the steps of:

(a) providing a glyoxal solution and adding thereto a base in an amount sufficient to neutralize acids which may be contained in said glyoxal solution;

(b) adding said glyoxal solution to a reaction solution containing benzylamine, perchloric acid, and a polar organic solvent which is substantially nonreactive with the glyoxal and the benzyl amine (c) allowing the glyoxal and the benzylamine to react and form HBIW; and (d) isolating the HBIW.

* * * * *